(12) United States Patent
Pfaff et al.

(10) Patent No.: US 12,396,797 B2
(45) Date of Patent: Aug. 26, 2025

(54) SYSTEM AND METHODS OF MANUFACTURING A LATERAL MENISCUS IMPLANT

(71) Applicant: Rutgers, The State University of New Jersey, New Brunswick, NJ (US)

(72) Inventors: William Pfaff, Chester, NJ (US); Michael G. Dunn, Manalapan, NJ (US); Charles J. Gatt, Jr., Skillman, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 18/835,973

(22) PCT Filed: Feb. 3, 2023

(86) PCT No.: PCT/US2023/061970
§ 371 (c)(1),
(2) Date: Aug. 5, 2024

(87) PCT Pub. No.: WO2023/150701
PCT Pub. Date: Aug. 10, 2023

(65) Prior Publication Data
US 2025/0134595 A1      May 1, 2025

Related U.S. Application Data (60) Provisional application No. 63/267,559, filed on Feb. 4, 2022.

(51) Int. Cl.
*A61B 34/10* (2016.01)
*A61F 2/30* (2006.01)

(52) U.S. Cl.
CPC .......... *A61B 34/10* (2016.02); *A61F 2/30942* (2013.01); *A61B 2034/104* (2016.02);
(Continued)

(58) Field of Classification Search
CPC .............. A61B 34/10; A61B 2034/104; A61B 2034/105; A61F 2/30942; A61F 2002/30784
See application file for complete search history.

(56) References Cited

U.S. PATENT DOCUMENTS

| | | |
|---|---|---|
| 2004/0133275 A1 | 7/2004 | Mansmann |
| 2007/0041952 A1 | 2/2007 | Guilak et al. |

(Continued)

OTHER PUBLICATIONS

International Search Report and Written Opinion for Application No. PCT/US23/61970 and issued on Jun. 22, 2023 (9 pp).

*Primary Examiner* — Gary Collins
(74) *Attorney, Agent, or Firm* — FOX ROTHSCHILD LLP (57) ABSTRACT

A method for forming a scaffold for use in fabricating a soft tissue implant, comprising: receiving, by a processor, soft tissue data corresponding to dimensions for a soft tissue, and a first and second weighting factor selected based on the dimensions of the soft tissue; transforming, by the processor, the soft tissue data, based on the first and second weighting factors, into a plurality of pin coordinates in a multi-dimensional space defining a shape of the scaffold for use in fabricating the soft tissue implant; and providing, by the processor, instructions to form the scaffold using weaving operations based on the pin coordinates.

20 Claims, 6 Drawing Sheets

(52) U.S. Cl.
CPC .................. *A61B 2034/105* (2016.02); *A61F 2002/30784* (2013.01)

(56) References Cited

U.S. PATENT DOCUMENTS

| | | |
|---|---|---|
| 2012/0041446 A1 | 2/2012 | Wong et al. |
| 2014/0244220 A1 | 8/2014 | McKinnon et al. |
| 2018/0360610 A1* | 12/2018 | Patel ..................... A61F 2/3872 |
| 2020/0330647 A1* | 10/2020 | Wadsworth ............ A61L 27/26 |
| 2022/0008209 A1 | 1/2022 | Ghodbane et al. |

* cited by examiner

```
┌─────────────────────────────────────────────────────────────────────────────┐
│ Receive, by a processor, soft tissue data corresponding to dimensions for a │
│ soft tissue, and a first and second weighting factor selected based on the  │
│ dimensions of the soft tissue                                               │
│                                                                        2010 │
└─────────────────────────────────────────────────────────────────────────────┘
                                     │
                                     ▼
┌─────────────────────────────────────────────────────────────────────────────┐
│ Transform, by the processor, the soft tissue data, based on the first and   │
│ second weighting factors, into a plurality of pin coordinates in a multi-   │
│ dimensional space defining a shape of the scaffold for use in fabricating   │
│ the soft tissue implant                                                2020 │
└─────────────────────────────────────────────────────────────────────────────┘
                                     │
                                     ▼
┌─────────────────────────────────────────────────────────────────────────────┐
│ Providing, by the processor, instructions to form the scaffold using        │
│ weaving operations based on the pin coordinates                             │
│                                                                        2030 │
└─────────────────────────────────────────────────────────────────────────────┘
```

FIG. 6

SYSTEM AND METHODS OF MANUFACTURING A LATERAL MENISCUS IMPLANT

CLAIM OF PRIORITY

The present application is the U.S. National Phase of International Patent Application No. PCT/US23/61970, filed Feb. 3, 2023, which claims priority to U.S. Provisional Application No. 63/267,559 filed Feb. 4, 2022, the entire disclosures of which are incorporated herein in their entirety.

BACKGROUND OF THE INVENTION

Meniscus injuries are common in the general population due to workplace accidents and sports related activities. Where the meniscal injuries are extensive, one method of treatment includes the use of a biocompatible, resorbable meniscus replacement to replace damaged meniscal tissue. This meniscus replacement is a fiber-reinforced meniscus scaffold having an intricate internal shape that can bear circumferential tensile loads. The strength of the scaffold is due to the many intersecting fiber reinforcements that distribute weight throughout the structure. This artificial weight-bearing tissue has a great potential in treating meniscus injuries.

While methods exist for construction of a medial meniscal implant, current systems and methods are unable to manufacture a lateral meniscal implant that has the same dimensions and mechanics of the native lateral meniscus of a subject. This is because of the differences manifested in the width of the middle portion of the native lateral meniscus, which is independent of the width of the anterior and posterior horn, as well as because of the difference in the orientation of the anterior and posterior tails of a native lateral meniscal implant. For example, in a native lateral meniscus the posterior horn is wider than the anterior horn, and current methods of manufacturing a meniscus implant are unable to form an implant having a variable width along its body.

The present disclosure provides for a method of manufacturing a meniscus implant addressing these noted issues.

BRIEF SUMMARY OF THE INVENTION

One aspect of the disclosure provides for a method for forming a scaffold for use in fabricating a soft tissue implant, comprising: receiving, by a processor, soft tissue data corresponding to dimensions for a soft tissue, and a first and second weighting factor selected based on the dimensions of the soft tissue; transforming, by the processor, the soft tissue data, based on the first and second weighting factors, into a plurality of pin coordinates in a multi-dimensional space defining a shape of the scaffold for use in fabricating the soft tissue implant; and providing, by the processor, instructions to form the scaffold using weaving operations based on the pin coordinates. The first and second weighting factor can be selected based on a width of an anterior horn of the soft tissue, a width of a posterior horn of the soft tissue, and a width of a midbody of the soft tissue. The first weighting factor can be selected to correspond to a desired spacing between the pins in the pin coordinates in an anterior-posterior direction and the second weighting factor is selected to correspond to a desired spacing between the pins in the pin coordinates in a medial-lateral direction. The pin coordinates can define the scaffold to have an anterior tail and an anterior horn, the anterior tail being at a transverse angle to the anterior horn to define a bend between the anterior tail and the anterior horn. The pin coordinates can include an anchor pin coordinate at the bend for the placement of an anchor pin. The pin coordinates can define the scaffold to have a posterior tail and a posterior horn, the posterior tail being substantially in line with the posterior horn. The method can further comprise optimizing the first and second weighting factors by comparing the soft tissue data to dimensions of a simulated scaffold. Optimizing the first and second weighting factors can include using a root-mean-square error algorithm to minimize an error between the soft tissue data and the dimensions of the simulated scaffold. The method can further comprise adjusting the pin coordinates path based on the adjusted first and second weighting factors. Transforming the soft tissue data into the plurality of pin coordinates can also be based on a number of total pins desired to be used. Transforming the soft tissue data into the plurality of pin coordinates can also be based on a number of pins in a weave pattern. Optionally, the soft tissue implant is a lateral meniscal implant.

Another aspect of the disclosure provides for a system comprising: one or more computing devices; and a memory storing instructions, the one or more computing devices configured to execute the instructions to: receive soft tissue data corresponding to dimensions for a soft tissue, and a first and second weighting factor selected based on the dimensions of the soft tissue; transform the soft tissue data, based on the first and second weighting factors, into a plurality of pin coordinates in a multi-dimensional space defining a shape of the scaffold for use in fabricating the soft tissue implant; and provide instructions to form the scaffold using weaving operations based on the pin coordinates. The first and second weighting factor can be selected based on a width of an anterior horn of the soft tissue, a width of a posterior horn of the soft tissue, and a width of a midbody of the soft tissue. The first weighting factor can be selected to correspond to a desired spacing between the pins in the pin coordinates in an anterior-posterior direction and the second weighting factor is selected to correspond to a desired spacing between the pins in the pin coordinates in a medial-lateral direction. The pin coordinates can define the scaffold to have an anterior tail and an anterior horn, the anterior tail being at a transverse angle to the anterior horn to define a bend between the anterior tail and the anterior horn. The pin coordinates can include an anchor pin coordinate at the bend for the placement of an anchor pin. The pin coordinates can define the scaffold to have a posterior tail and a posterior horn, the posterior tail being substantially in line with the posterior horn. The method can further comprise optimizing the first and second weighting factors by comparing the soft tissue data to dimensions of a simulated scaffold. The method can further comprise adjusting the pin coordinates path based on the adjusted first and second weighting factors.

Yet another aspect of the disclosure provides for a non-transitory computing-device readable storage medium on which computing-device readable instructions of a program are stored, the instructions, when executed by one or more computing devices, causing the one or more computing devices to perform a method, the method comprising: receiving soft tissue data corresponding to dimensions for a soft tissue, and a first and second weighting factor selected based on the dimensions of the soft tissue; transforming the soft tissue data, based on the first and second weighting factors, into a plurality of pin coordinates in a multi-dimensional space defining a shape of the scaffold for use in fabricating the soft tissue implant; and providing instructions to form the scaffold using weaving operations based on the pin coordinates. The pin coordinates can define the scaffold to have an anterior tail and an anterior horn, the anterior tail being at a transverse angle to the anterior horn to define a bend between the anterior tail and the anterior horn.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION OF THE INVENTION

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Figure 1:
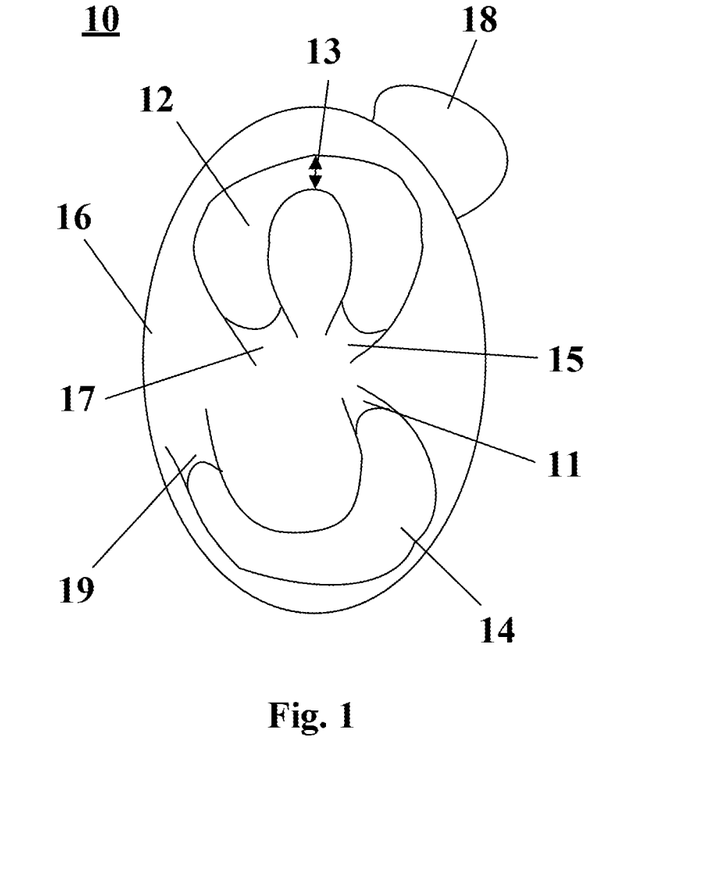
FIG. 1 depicts an illustrative view of an example knee anatomy.

As discussed above, construction of a lateral meniscal implant requires consideration of the differences between the lateral meniscus and the medial meniscus morphology. One of these differences is manifested in the width of the middle portion of the lateral meniscus, which is independent of the width of the anterior and posterior horn and requires an optimization between at least two weighting factors instead of one (as is the case in medial meniscal implants). The other difference is the orientation of the anterior and posterior tails, which extend off the perimeter of the anterior and posterior horns without causing an overlap. Specifically, there is a need to manufacture a meniscus replacement that does not have a constant width or whose width does not have a constant change, without crisscrossing tails. With reference to FIG. 1, an example knee 10 is depicted showing a lateral meniscus 12, a medial meniscus 14, a tibia 16 at an anterior end of the knee 10, and a fibula 18 at a posterior end of the knee 10. As shown, medial meniscus 14 has a width that changes at a substantially constant rate along its length from an anterior end toward its posterior end. Prior methods are able to manufacture a meniscus implant for medial meniscus 14 due to this constant change in width over its length but have not been configured for manufacturing a meniscus implant where the width does not have a constant change along its length, such as for the lateral meniscus 12 with a section 13 along a midbody of the lateral meniscus 12 having a smaller width compared to the rest of the lateral meniscus 12.

Moreover, current methods of manufacturing implants with woven fibers are not configured for manufacturing a lateral meniscus implant. Such methods were designed to create a meniscus implant with tails in line with their respective horns and, when used to create a lateral meniscus implant, would result in an implant that has the posterior tail crossing over the anterior tail, which leads to issues during manufacturing the meniscus. With continued reference to FIG. 1, the lateral meniscus 12 has a posterior tail 15 and anterior tail 17 that cross over each other to provide a secured connection to the knee 10. While current methods can manufacture a meniscus implant for the medial meniscus 14 as its posterior tail 11 and anterior tail 19 do not intersect, such methods would have issues manufacturing a meniscus implant with crossing tails, such as for replacing the lateral meniscus 12, as the fibers for a fiber-reinforced meniscus scaffold would cross over each other during the formation of the tails and prevent separation of the tails.

The system and method of making a personalized implant will be described herein with respect to making of a soft tissue implant (e.g., knee lateral meniscus implant). Although the instant implant is described in relation to making of a knee meniscus implant, the teachings of the instant disclosure may also be applied to making implants for replacing other tissues similar in nature and function to the meniscus, such as intervertebral discs, temporomandibular discs, wrist menisci, and the like. These tissues are similar to the knee meniscus in that they are composed of fibrocartilage and function as load transmitters and distributors to prevent high-stress cartilage-on-cartilage or bone-on-bone contact that is detrimental to the joint. It will also be understood that the instant teachings may be applied to make implants for both human and animal patients. Additionally, the implant can be a tendon implant, a ligament implant and/or cartilage implant.

As will be described further below, manufacturing the implant includes at least one fiber woven about a set of pins to form a woven scaffold which is later injected with a polymer material within a mold to form the implant. As used herein, the term "fiber" refers to any generally elongated member consisting of a single component (e.g., monofilament suture) or multiple components (e.g., multifilament suture). The physical properties of the fiber (such as tensile strength, cross-sectional area, diameter, flexibility, etc.) may vary over the length of the fiber. In some scenarios, multiple fibers may be used to form the scaffold. In this instance, the fibers may be made of the same or different materials and may follow the same or different paths. The pins can be made of nitinol due to its chemical resistance and high stiffness, but can also be made of stainless steel or other sufficient stiff material.

The implant, including both the scaffold and the fibers, is generally constructed of naturally-occurring or synthetic biocompatible materials or a combination thereof so to enable infiltration, attachment and proliferation of cells from surrounding tissues once the implant is in place. The naturally-occurring or synthetic biocompatible materials may also be bioresorbable. The scaffold and the fibers may be constructed from the same material or different materials, and may be fully or partially biodegradable and may have the same or different rate of degradation.

As used herein, the term "synthetic polymer" refers to polymers that are not found in nature, even if the polymers are made from naturally occurring biomaterials. The term "natural polymer," as used herein, refers to polymers that are naturally occurring. The term "biocompatible," as used herein, refers to materials that, in the amounts employed, do not elicit a detrimental response in the host. The term "biocompatible," as used herein, is intended to include materials that may cause some inflammation, tissue necrosis or other immune responses when introduced into the host, provided that these effects do not rise to the level of pathogenesis. The term "bioresorbable," as used herein, refers to those materials that when placed in a living body at standard physiological conditions are degraded through either enzymatic, hydrolytic or other chemical reactions or cellular processes into by-products that are either integrated into or expelled from the body. It is recognized that in the literature, the terms "bioresorbable," "resorbable," "absorbable," "bioabsorbable," and "biodegradable" are frequently used interchangeably and such interchangeable meaning is intended for the present application. In some scenarios, the implant is formed from biodegradable material or materials. The polymers for the instant implant are selected so the implant possesses mechanical properties which are the same or substantially similar to the mechanical properties of the native tissue being replaced.

Examples of suitable natural polymers include, but are not limited to, collagen, hyaluronic acid, fibrin glue, bone marrow, chitosan, alginates, celluloses, starches, silk, elastin, and other animal- or plant-derived proteins or polysaccharides. Suitable synthetic polymers include, but are not limited to, poly(alpha-hydroxy acids), poly(lactide-co-glycolide) (PLGA), poly(L-lactides) (PLLA), polylactides (PLA), polyglycolides (PGA); polyethylene, polypropylene, polyvinyl alcohol (PVA), polyethylene oxide (PEO); poly-p-dioxanone (PDO); polyarylates, polyacrylates, polycarbonates, polyesters, polycaprolactone (PCL) and combinations thereof. Suitable polyarylates and polycarbonates include, but are not limited to the tyrosine-derived polyarylates and polycarbonates disclosed by U.S. Pat. Nos. 5,099,060, 5,198,507, 5,216,115, 5,587,507, 5,658,995 and 6,048,521 (the disclosures of all of which are incorporated herein by reference).

In some scenarios, the scaffold is an amorphous structure composed primarily of Type I collagen. In addition to collagen, other types of materials may be added to alter the scaffold's properties as necessary or desired. For example, other proteins or proteoglycans may be used, including, but not limited to, glycosaminoglycans such as chondroitin sulfate, keratan sulfate, dermatan sulfate, heparin, heparin sulfate and hyaluronic acid. The percentage of these materials in the scaffold may range between zero (0) and about twenty percent (20%) of the dry weight of the scaffold. The fiber may preferably be made from a bioresorbable synthetic polymer (such as a polyarylate), a non-synthetic material (such as collagen), or a fiber material (such as nylon).

The physical characteristics of the implant may be modified by using different materials for the scaffold and/or forming the scaffold from fibers of different diameter, mechanical strength, stiffness, or durability. Moreover, the physical characteristics of the implant may be modified by cross-linking various portions the scaffold. Cross-linking may be achieved by employing a variety of known methods including, but not limited to: chemical reaction with a carbodiimide, glutaraldehyde or formaldehyde among others; the application of energy such as radiant energy, which includes irradiation by UV light or microwave energy; dehydrothermal treatment in which water is slowly removed while the bone tissue is subjected to a vacuum; and enzymatic treatment.

The shape and geometry of the scaffold (and consequently the implant) is determined and customized based on the shape and geometry of the soft tissue in need of replacement. For example, in the case of a vertebral disc replacement, a scaffold having a toroidal shape that an interior cavity configured to receive a biocompatible material with physical properties equivalent to the properties of the nucleus pulposus of a patient's vertebral disc. One example of a toroidal implant is disclosed in U.S. Pat. No. 11,154,403 (the "'403 patent"), the disclosure of which is incorporated herein by reference.

However, in the case of a meniscus implant, the scaffold may be constructed as a C-shaped disc with a wedge-like cross-section (similarly to a knee meniscus). Furthermore, the scaffold may be shaped concave on a superior surface (which would contact a femur) and flat on an inferior surface (which would rest on the tibial plateau).

Figure 2:
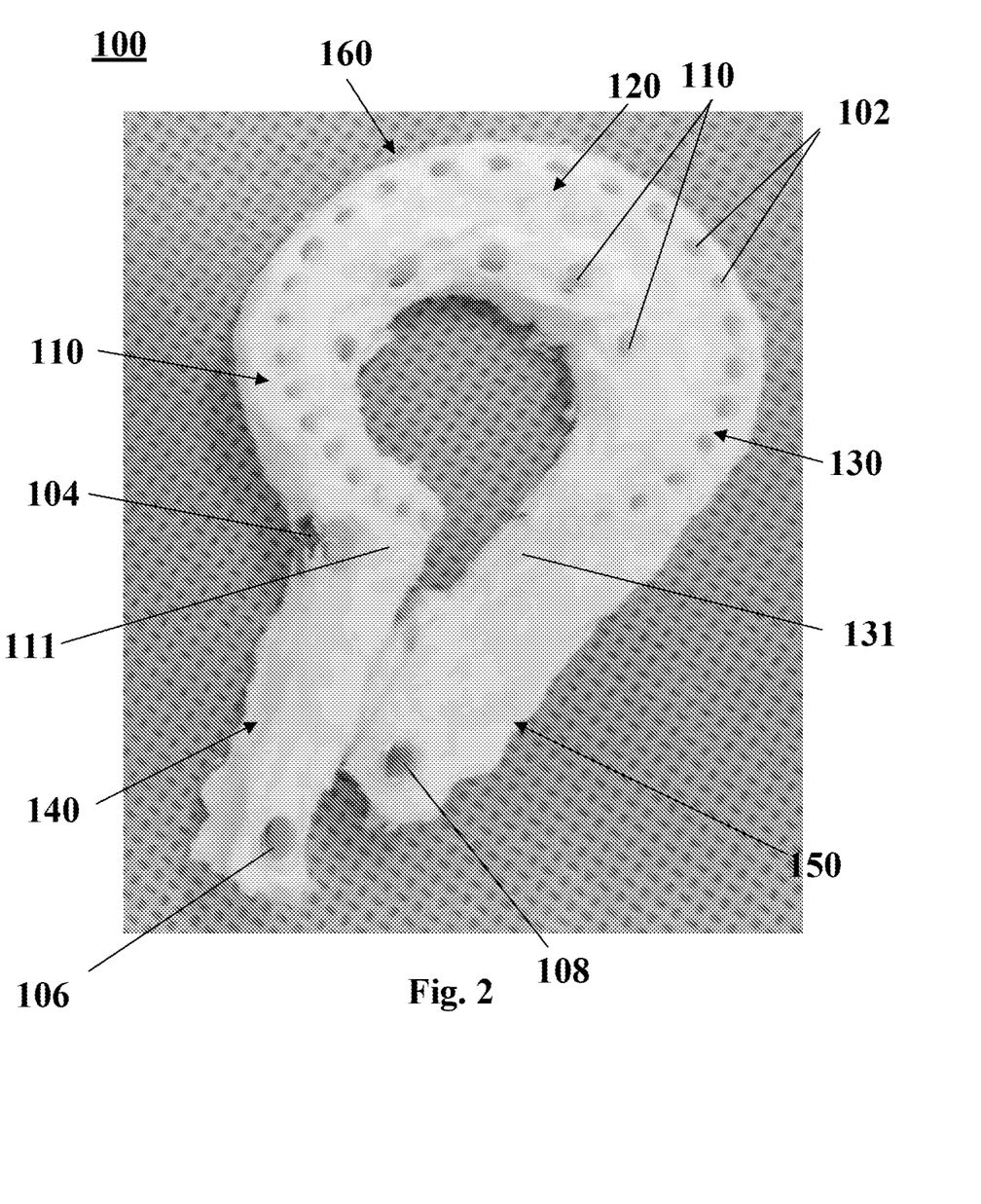
FIG. 2 depicts an example meniscus implant according to one aspect of the disclosure.

FIG. 2 depicts an example lateral meniscus implant 100 having a body 160 and tails 140, 150 extending therefrom. The body 160 has a length defined between anterior end 111 and posterior end 131. The body 160 includes an anterior horn 110, midbody 120, and posterior horn 130. As shown, each of the anterior horn 110, midbody 120, and posterior horn 130 have differing widths. Such widths can be adjusted during manufacture according to a patient's specific anatomy and the type of desired implant.

Anterior tail 140 extends from the anterior end 111 and the posterior tail 150 extends from the posterior end 131. The posterior tail 150 extends from the body 160 substantially in line with the posterior horn 130 while the anterior tail 140 extends from the body 160 at an angle transverse to the anterior horn 110 (e.g., about 90 degrees, about 80-90 degrees, about 90 to 100 degrees, or the like). As discussed further below, this accounts for the peculiarities of manufacturing the implant 100 using a fiber scaffold. However, in other embodiments, the angles of the anterior and posterior tail relative to the body can be reversed. In yet other embodiments, the anterior and posterior tail can have substantially the same angle relative to the body. For example, each of the anterior and posterior tails can be at a transverse angle to the body to form a bend.

This bend provides a number of structural benefits. For example, during implantation, when the tails 140, 150 are pulled through by the surgeon to seat the implant 100 onto a knee, the bend between the anterior tail 140 and the body 160 provides a tactile sensation to the surgeon, when the bend comes into contact with bone, that informs the surgeon when the body 160 is adequately seated within the knee. This ensures a more secure mechanical placement of the implant 100. Moreover, this bend helps dissipate the forces being applied along the implant 100 by directing circumferential hoop stresses into the anterior horn 210 when the implant 100 is in use by the patient after its implantation. The bend, therefore, assists in more equally distributing the forces along the implant 100 rather than having the forces concentrate on a specific point along the implant 100 that can result in an increased chance of mechanical failure at that point. The bend provides such benefits with a negligible loss of mechanical integrity to the implant 100.

The implant 100 defines holes 102, 104, 106, 108. Each of the holes are sized to a pin previously used to manufacture the implant 100. As will be discussed further below, the size, shape, and location of the holes 102, 104, 106, 108 are dependent on the size, shape, and location of the pins during manufacturing of the implant 100.

In other examples, the implant can have a porosity designed in accordance with a particular application. For example, the implant can be designed to have a relatively high porosity to ensure adequate tissue and cell infiltration therethrough. Any level of porosity can be used herein without limitation provided that is sufficient for facilitating adequate cell seeding, fluid flow and structural integrity.

Figure 3:
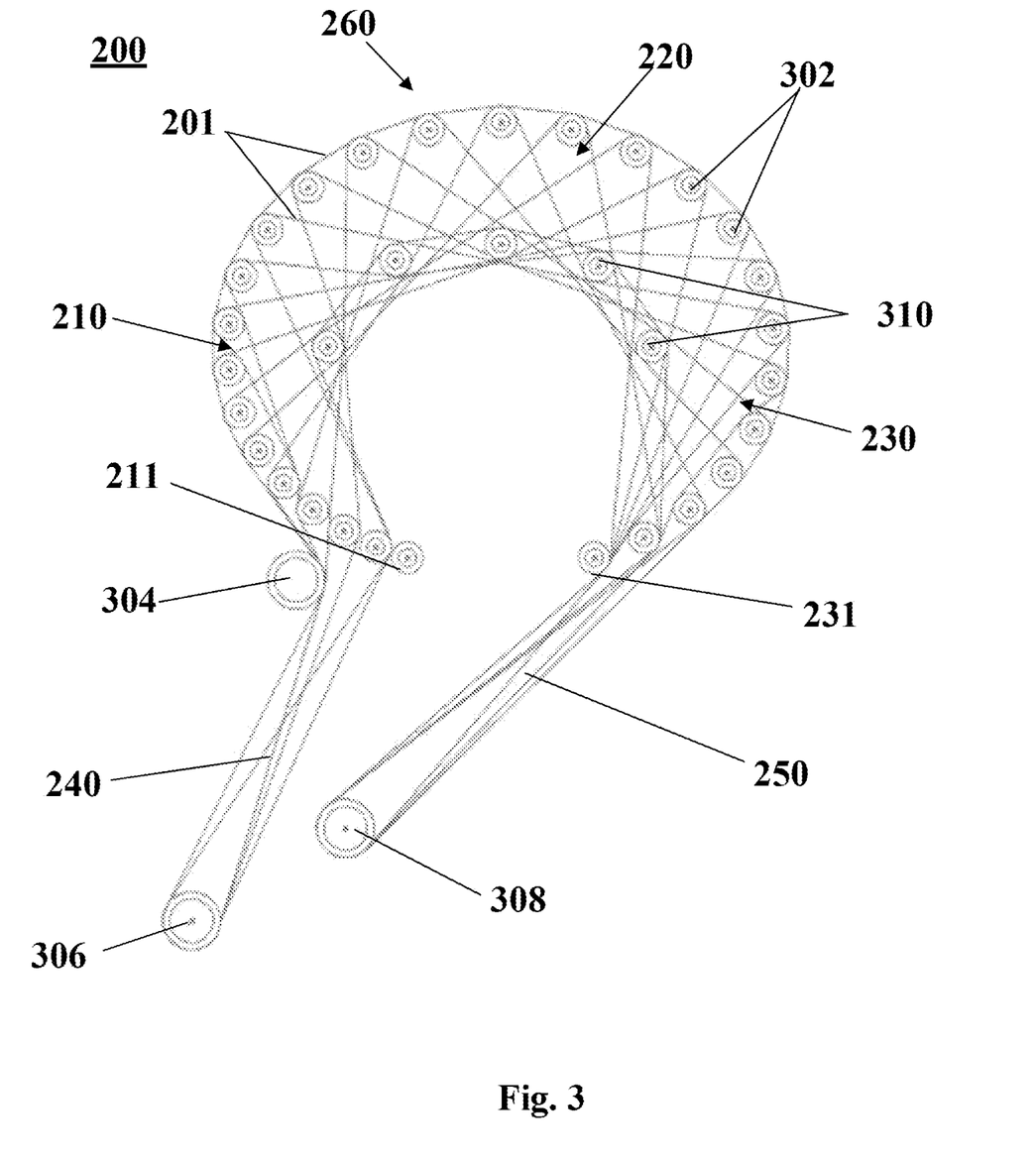
FIG. 3 depicts an example scaffold used to form the implant of FIG. 2.

To manufacture the implant 100, the dimensions of the lateral meniscus is first acquired through conventional methods known in the art (e.g., imaging of the meniscal tissue to be replaced for creation of a personalized meniscus implant, using average meniscal dimensions based on age, sex, etc., for creation of one or more standard size meniscal implants, or the like). After the dimensions are determined, a position of pins (or nodes) are determined to allow for fiber to woven about the pins and to form a scaffold. For example, FIG. 2 depicts an example scaffold 200 for use in manufacturing the implant 100. The scaffold 200 is made of fiber 201 woven about circumference pins 302, anchor pin 304, anterior attachment pin 306, posterior attachment pin 308, and interior pins 310. The scaffold 200 includes a body 260 with an anterior tail 240 and a posterior tail 250 extending therefrom. The body 260 of the scaffold 200 has a length which extends from an anterior end 211 to posterior end 231. The body 260 is defined by a 9 pattern weave (denoting the number of circumference pins 302 that the fiber 201 skips after engaging with a first outer circumference pin 302) across 25 circumference pins 302 that act as nodes around which the fiber is wound (i.e., not counting the two end circumference pins 302). The body 260 includes an anterior horn 210, midbody 220, and posterior horn 230. The anterior tail 240 extends from an anterior end 211 of the body 260 and the posterior tail 250 extends from a posterior end 231 of the body 260.

Circumference pins 302 extend along an outer circumference of the scaffold 200 from the anterior end 211 to the posterior end 231 to define the outer-most side of the scaffold 200 while the interior pins 310 extend along an inner circumference of the scaffold 200 from the anterior end 211 to the posterior end 231. The interior pins 310 are positioned to support weaving of the scaffold 200 such that the woven fabric defines an inner-most side of the scaffold 200. Attachment pins 306, 308 extend a distance away from the pins 302, 310 defining the body 260 to allow for the fiber 201 to be wrapped around and form the tails 240, 250.

Anchor pin 304 facilitates formation of the transverse angle between the anterior tail 240 and the anterior horn 210 by allowing for a portion of the fiber 201 to wrap around the anchor pin 304. As the increased height and density of stacked fiber 201 required to form the angle between the anterior tail 240 and anterior horn 210 can bend or break pins 302, the anchor pin 304 can be larger in both circumference and height, as well as being a more structurally stiff material, than pins 302 (e.g., stainless steel for anchor pin 304 rather than nitinol for the pins 302). This structural difference allows for the anchor pin 304 to withstand the increased forces associated with an increased fiber density at that point than pins 302.

The pins 302, 304, 306, 308, 310 are arranged to provide a location where the fiber 201 can be wrapped about during manufacturing in accordance with the desired shape and size of the implant 100. Specifically, the location of the circumference pins 302 are positioned to determine the widths of the anterior horn 210, midbody 220, and posterior horn 230. The position of the circumference pins 302 can be determined based on the following mathematical equations:

Mathematical Equation 1

$$\Theta\left(x_{2 \to n_{mid}}\right) = \Theta(x-1) + \frac{\Theta(n) - \Theta(1)}{(n-1)} - \qquad \text{(``Equation 1'')}$$
$$W_{AP} * \left(\frac{n}{2} - x + 1\right) + W_{ML} * \left(\frac{n_{mid}}{2} + 1 - n\right)$$

Mathematical Equation 2

$$\Theta\left(x_{n_{mid} \to n}\right) = \Theta(x-1) + \frac{\Theta(n) - \Theta(1)}{(n-1)} - \qquad \text{(``Equation 2'')}$$
$$W_{AP} * \left(\frac{n}{2} - x + 1\right) - W_{ML} * \left(\frac{n_{mid}}{2} + 1 - (n - n_{mid})\right)$$

n represents the number of pins while $n_{mid}$ represents the median pin number of the n pins. Equation 1 determines the angular coordinates for the circumference pin for a first half of a meniscus implant (e.g., the anterior half of the implant) while Equation 2 determines the angular coordinates for the circumference pin for a second half of a meniscus implant (e.g., the posterior half of the implant). $\Theta(1)$ represents the angular position of the circumference at the anterior end of the scaffold, (n) represents the angular position of the circumference at the posterior end of the scaffold, $\Theta(x_{n_{mid}})$ represents the angular position of the circumference at the median point of the scaffold (at the middle of the midbody of the scaffold) between the anterior and posterior ends, and $\Theta(x)$ represents the angular position of the $x^{th}$ circumference pin. $W_{AP}$ represents the weighting factor that adjusts the spacing between pins in an anterior-posterior direction while $W_{ML}$ represents the weighting factor that adjusts the spacing between pins in a medial-lateral direction. $W_{AP}$ and $W_{ML}$ ranges from −1 to 1.

Equations 1 and 2 determines the pin coordinates for the pin to be placed in a position that allows for the width of the anterior horn, posterior horn, and midbody of a meniscal implant to be independently changed. In particular, changing the values of the two weighting factors $W_{AP}$, $W_{ML}$ changes the spacing and location of the interior pins 310 relative to the circumference pins 302 along the anterior-posterior and medial-lateral directions which, in turn, individually changes the widths of the anterior horn, posterior horn, and midbody. As such, depending on the values of the two weighting factors $W_{AP}$, $W_{ML}$, certain of the interior pins 310 can be closer or farther from the circumference pins 302 to define the widths along the implant 100.

For instance, turning to FIGS. 4A-D, simulated bodies 460A-D for a scaffold are depicted. These simulated bodies 460A-D depict a 9 pattern weave across 25 total circumference pins with various widths across their anterior horn 410A-D, midbody 420A-D, and posterior horn 430A-D depending on the specific weighting factors for each of the simulated bodies 460A-D.

Figures 4A, 4B:
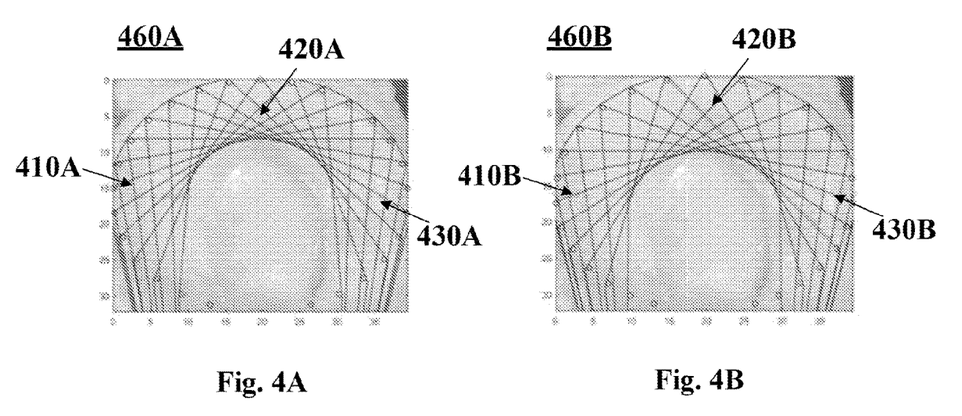
FIG. 4 depicts example simulated bodies for use in optimizing the dimensions of the scaffold, in accordance with another aspect of the disclosure.
Figures 4C, 4D:
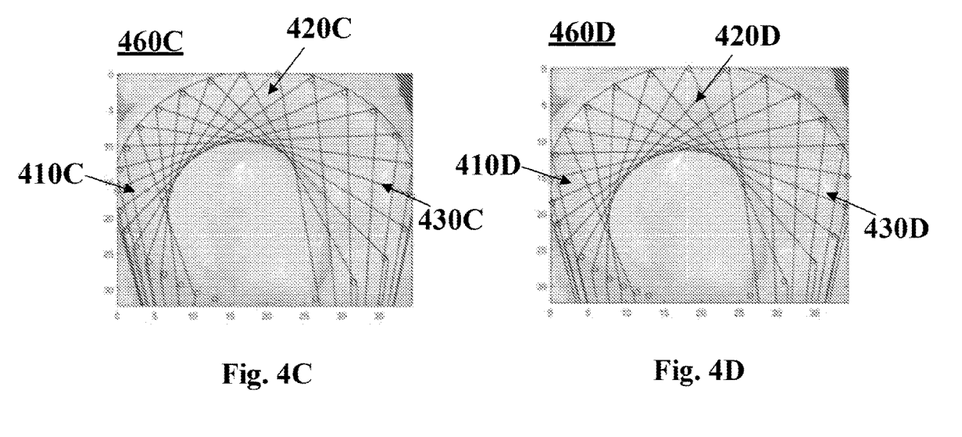

Specifically, FIG. 3A depicts a simulated bodies 460A-D with a $W_{AP}$ of 0 and $W_{ML}$ of 0. FIG. 4B depicts a simulated bodies 460A-D with a $W_{AP}$ of 0 and $W_{ML}$ of −0.4. FIG. 3C depicts a simulated bodies 460A-D with a $W_{AP}$ of 0.4 and $W_{ML}$ of 0. FIG. 3D depicts a simulated bodies 460A-D with a $W_{AP}$ of 0.4 and $W_{ML}$ of −0.4. As such, by changing the weighting factors for Equations 1 and 2, the placement of pins can be used to create a scaffold (and, afterwards, an implant) to account for a varying degree of widths along a meniscus to be replaced. This ability to customize the widths of the anterior horn, posterior horn, and midbody independent of each other is an improvement over prior art methods of manufacturing implants.

The specific number of pins (n), the number of pins for the weave pattern, and the two weighting factors ($W_{AP}$ and $W_{ML}$) can be optimally determined by simulating a meniscus implant over a range of values for the above inputs. Once the simulated meniscus is formed, the widths of the simulated anterior horn, midbody, and posterior horn can be optimized by using the following root-mean-square (RMS) equation to determine the input values with the lowest RMS error by comparing the desired dimensions for the implant with dimensions for various simulated implants.

$$RMS_{Error} = \sqrt{(A_{des} - A_{sim})^2 \mp (B_{des} - B_{sim})^2 \mp (P_{des} - P_{sim})^2}$$

$RMS_{Error}$ represents a RMS error, Ades represents a desired width of the anterior horn, $A_{sim}$ represents the simulated width of the anterior horn, $B_{des}$ represents a desired width of the midbody, $B_{sim}$ represents the simulated width of the midbody, $P_{des}$ represents a desired width of the posterior horn, and $P_{sim}$ represents the simulated width of the posterior horn.

As one example of optimization, the dimensions of the simulated bodies 460A-D can be compared to the desired dimensions for an implant (e.g., the dimensions of the meniscus to be replaced) using the RMS equation to determine the optimal weighting factors for an implant having given a certain pattern weave and total circumference pins (e.g., 9 pattern weave across 25 total circumference pins). A similar analysis can be done for the number of pattern weave and the total amount of circumference pins to be used.

Note that this optimization cannot set the number of pins so high as to inhibit manufacturing of the implant. For example, having too many pins can result in the space between each pin being so small as to prevent the needle carrying the fabric from passing between each pin. As such, there is an upper limit on the maximum amount of pins for use during manufacturing.

Turning back to FIG. 3, the coordinates of the anchor pin 304 and attachments pins 306, 308 are chosen to provide a transverse angle (or bend) between the anterior tail 240 and the body 260 while leaving the posterior tail 250 substantially in line with the posterior horn 230. Aside from the structural benefits that the bend provides, as noted above, such an angle is chosen to accommodate current surgical techniques. According to existing surgical technique, the bone tunnel for fixing a lateral meniscus implant on the anterior side is at a 90 degree angle perpendicular to the surface of the tibial plateau whereas the bone tunnel on the posterior side is generally in line with the root. As such, the bend is positioned on the anterior side because such a bend is adapted for established surgical technique. However, as noted above, in other embodiments, the bend can be formed along the posterior portion of the implant 100 (or there can be no bend at all) depending on the surgeon's preference.

Further, the bend addresses issues resulting from attempting to manufacture a lateral meniscus implant using traditional methods. As depicted in FIG. 1, the horns of the native lateral meniscus are angled towards each other and the tails extend in line from their corresponding horns. As the manufactured meniscus implant requires the tails to be of sufficient length for implantation, attempting to manufacture an implant using traditional manufacturing methods to mirror the native lateral meniscus would result in the tails crossing over each other. Since these tails are formed of stacked woven fibers, such crisscrossed tails cannot be separated and utilized for implantation. As such, the transverse angle between the anterior tail 240 and the body 260, provides for the manufacturing benefit of allowing the posterior tail 250 to maintain its angular alignment with the posterior horn 230 as a natural lateral meniscus would have while allowing for the anterior tail 240 to be a separate portion for the surgeon to manipulate once the scaffold 200 is formed into the implant 100 (e.g., the anterior tail 140). Further, the bend allows for the horns 210, 230 to be placed closer together than would previously be permitted with traditional manufacturing techniques, thus mirroring the physiology and function of the native lateral meniscus.

As discussed above, the size, structure, and position of the anchor pin 304 is chosen to facilitate the formation of the transverse angle between the anterior tail 240 and the body 260. However, in other embodiments, where the posterior tail is additionally or alternatively chosen to have a transverse angle with respect to the body, an anchor pin can be correspondingly placed adjacent the posterior end of the body to help define the transverse angle between the posterior tail and the body.

After all the pins 302, 304, 306, 308, 310 are positioned, the fiber 201 can be woven about the pins 302, 304, 306, 308, 310 to form the scaffold based on a construction path using a method similar to that disclosed in the '403 patent. The fiber 201 can be woven using a needle engaged to a computer numerical control (CNC) machine. The CNC machine can weave the fiber 201 about the pins a desired amount of times at a desired frequency to achieve a particular density of the fibers 201. Once the scaffold 200 is formed, the scaffold 200 is injected with a polymer, lyophilized, trimmed, cross-linked, and rinsed using methods known in the art to from the implant 100.

Figure 5:
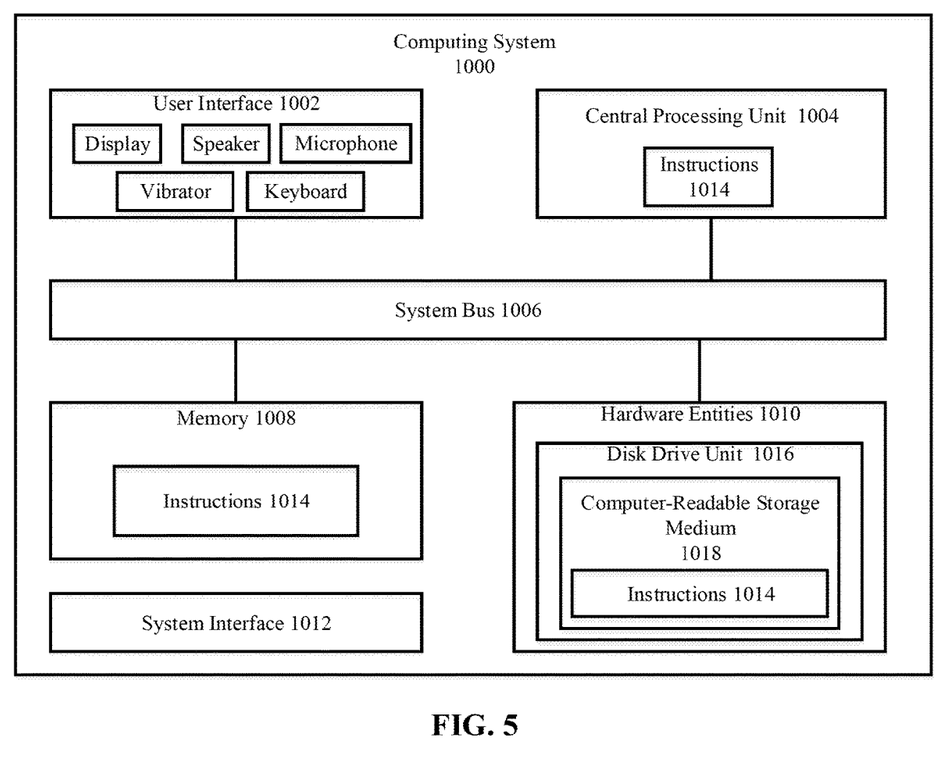
FIG. 5 depicts an example system in accordance with another aspect of the disclosure.

Referring now to FIG. 5, there is provided a schematic illustration an exemplary computing device 1000. The computing device can include, but is not limited to, a personal computer, a laptop computer, a desktop computer and/or a server. The computing device 1000 is generally configured to perform operations for facilitating the generation of an implant (e.g., the implant 100 of FIG. 2). As such, the computing system 1000 comprises a plurality of components 1002-1012. The computing system 1000 can include more or less components than those shown in FIG. 5. However, the components shown are sufficient to disclose an illustrative embodiment implementing the present solution. Notably, the hardware shown in FIG. 5 can include physical hardware and/or virtual hardware.

The hardware architecture of FIG. 5 represents one (1) embodiment of a representative computing device configured to facilitate the generation of an implant (e.g., the implant 100 of FIG. 2). As such, the computing system 1000 implements methods of the present solution.

As shown in FIG. 10, the computing system 1000 includes a system interface 1012, a user interface 1002 (e.g., a keyboard for data input and a display for data output), a Central Processing Unit ("CPU") 1004, a system bus 1006, a memory 1008 connected to and accessible by other portions of the computing system 1000 through system bus 1006, and hardware entities 1010 connected to system bus 1006. System bus 1006 is also used to communicate one or more mission plans to and from the computing system 1000. At least some of the hardware entities 1010 perform actions involving access to and use of memory 1008, which can be a Random Access Memory ("RAM"), a disk driver and/or a Compact Disc Read Only Memory ("CD-ROM"). System interface 1012 allows the computing system 1000 to communicate directly or indirectly with external devices (e.g., sensors, servers and client computers).

Hardware entities 1010 can include microprocessors, Application Specific Integrated Circuits ("ASICs") and other hardware. Hardware entities 1010 can include a microprocessor programmed to facilitate the generation of an implant (e.g., the implant 100 of FIG. 2).

As shown in FIG. 5, the hardware entities 1010 can include a disk drive unit 1016 comprising a computer-readable storage medium 1018 on which is stored one or more sets of instructions (or programming instructions) 1014 (e.g., software code) configured to implement one or more of the methodologies, procedures, or functions described herein. The instructions 1014 can also reside, completely or at least partially, within the memory 1008 and/or the CPU 1004 during execution thereof by the computing device 1000. The components 1008 and 1004 also can constitute machine-readable media. The term "machine-readable media", as used here, refers to a single medium or multiple media (e.g., a centralized or distributed database, and/or associated caches and servers) that store the one or more sets of instructions 1014. The term "machine-readable media", as used here, also refers to any medium that is capable of storing, encoding or carrying a set of instructions 1014 for execution by the computing device 1000 and that cause the computing device 1000 to perform any one or more of the methodologies of the present disclosure.

Notably, the present solution can be implemented in a single computing device as shown in FIG. 5. The present solution is not limited in this regard. Alternatively, the present solution can be implemented in a distributed network system. For example, the present solution can take advantage of multiple CPU cores over a distributed network of computing devices in a cloud or cloud-like environment. The distributed network architecture ensures that the computing time of the statistics and enhanced functionality is reduced to a minimum, allowing end-users to perform more queries and to receive reports at a faster rate. The distributed network architecture also ensures that the implementing software is ready for being deployed on an organization's internal servers or on cloud services in order to take advantage of its scaling abilities (e.g., request more or less CPU cores dynamically as a function of the quantity of data to process or the number of parameters to evaluate).

Figure 6:
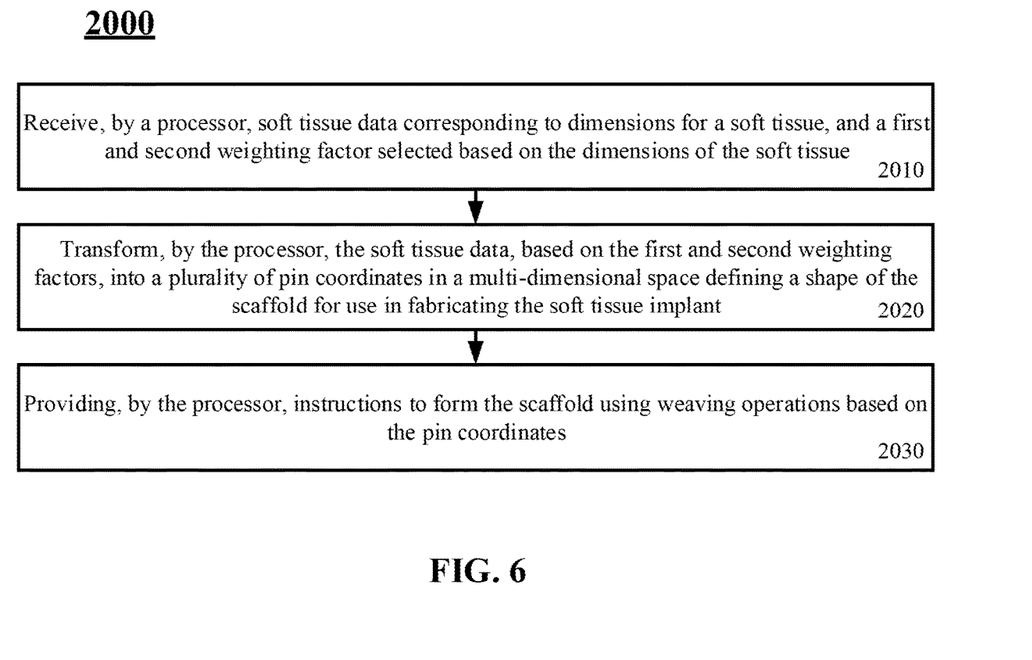
FIG. 6 depicts an example flowchart of a method in accordance with another aspect of the disclosure.

Referring now to FIG. 6, there is provided a flow diagram 2000 of an exemplary method for forming a scaffold (e.g., the scaffold 200 of FIG. 3) for use in fabricating a soft tissue implant (e.g., the implant 100 of FIG. 1). The method 2000 can be implemented by computing system 1000 of FIG. 5.

At step 2010, the CPU 1004 can receive soft tissue data corresponding to dimensions for a soft tissue (e.g., a target meniscus to be replaced), and a first weighting factor (e.g., $W_{AP}$) and a second weighting factor (e.g., $W_{ML}$) selected based on the dimensions of the soft tissue. Specifically, the first and second weighting factors can be initially chosen based on the widths of the anterior horn, the posterior horn, and the midbody.

At step 2020, the CPU 1004 can transform the soft tissue data, based on the first weighting factor and the second weighting factor, into a plurality of pin coordinates in a multi-dimensional space defining a shape of the scaffold 200 for use in fabricating the soft tissue implant 100 (e.g., the placement of the circumference pins 302 and interior pins 310). The pin coordinates include coordinates to place the pins 306, 308 to form the anterior tail 240 and posterior tail 250, as well as the coordinate to position the anchor pin 304 to facilitate the bend between the anterior tail 240 and the body 260. The CPU 1004 can additionally generate the pin coordinates based on the number of pins desired to be used in the scaffold and the number of pins for the weave pattern.

The CPU 1004 can optimize the first and second weighting factors by comparing the soft tissue data to dimensions of a simulated scaffold. For example, the CPU 1004 can simulate a scaffold for a range of first and second weighting factors (as well as the number of pins desired to be used in the scaffold and the number of pins for the weave pattern) and determine which simulation has the lowest RMS error using an RMS equation. The CPU 1004 can adjust the pin coordinates based on the inputs (i.e., the weighting factors, the number of weave pattern, and total circumference pins) of that simulation.

At step 2030, the CPU 1004 can provide instructions to form the scaffold using weaving operations based on the pin coordinates.

Although the disclosure herein has been described with reference to particular aspects, it is to be understood that these aspects are merely illustrative of the principles and applications of the present disclosure. It is therefore to be understood that numerous modifications may be made to the illustrative aspects and that other arrangements may be devised without departing from the spirit and scope of the present disclosure as defined by the appended claims.

What is claimed is:

1. A method for forming a scaffold for use in fabricating a soft tissue implant, comprising:
   receiving, by a processor, soft tissue data corresponding to dimensions for a soft tissue, and a first and second weighting factor selected based on the dimensions of the soft tissue;
   transforming, by the processor, the soft tissue data, based on the first and second weighting factors, into a plurality of pin coordinates in a multi-dimensional space defining a shape of the scaffold for use in fabricating the soft tissue implant; and
   providing, by the processor, instructions to form the scaffold using weaving operations based on the pin coordinates.

2. The method of claim 1, wherein the first and second weighting factor were selected based on a width of an anterior horn of the soft tissue, a width of a posterior horn of the soft tissue, and a width of a midbody of the soft tissue.

3. The method of claim 1, wherein the first weighting factor is selected to correspond to a desired spacing between the pins in the pin coordinates in an anterior-posterior direction and the second weighting factor is selected to correspond to a desired spacing between the pins in the pin coordinates in a medial-lateral direction.

4. The method of claim 1, wherein the pin coordinates define the scaffold to have an anterior tail and an anterior horn, the anterior tail being at a transverse angle to the anterior horn to define a bend between the anterior tail and the anterior horn.

5. The method of claim 4, wherein the pin coordinates define the scaffold to have a posterior tail and a posterior horn, the posterior tail being substantially in line with the posterior horn.

6. The system of claim 4, wherein the pin coordinates includes an anchor pin coordinate at the bend for the placement of an anchor pin.

7. The method of claim 1, further comprising optimizing the first and second weighting factors by comparing the soft tissue data to dimensions of a simulated scaffold.

8. The method of claim 6, wherein optimizing the first and second weighting factors includes using a root-mean-square error algorithm to minimize an error between the soft tissue data and the dimensions of the simulated scaffold.

9. The method of claim 7, further comprising adjusting the pin coordinates path based on the adjusted first and second weighting factors.

10. The method of claim 1, wherein transforming the soft tissue data into the plurality of pin coordinates is also based on a number of total pins desired to be used.

11. The method of claim 1, wherein transforming the soft tissue data into the plurality of pin coordinates is also based on a number of pins in a weave pattern.

12. The method of claim 1, wherein the soft tissue implant is a lateral meniscal implant.

13. A system comprising:
one or more computing devices; and
a memory storing instructions, the one or more computing devices configured to execute the instructions to:
receive soft tissue data corresponding to dimensions for a soft tissue, and a first and second weighting factor selected based on the dimensions of the soft tissue;
transform the soft tissue data, based on the first and second weighting factors, into a plurality of pin coordinates in a multi-dimensional space defining a shape of the scaffold for use in fabricating the soft tissue implant; and
provide instructions to form the scaffold using weaving operations based on the pin coordinates.

14. The system of claim 13, wherein the first and second weighting factor were selected based on a width of an anterior horn of the soft tissue, a width of a posterior horn of the soft tissue, and a width of a midbody of the soft tissue.

15. The system of claim 13, wherein the first weighting factor is selected to correspond to a desired spacing between the pins in the pin coordinates in an anterior-posterior direction and the second weighting factor is selected to correspond to a desired spacing between the pins in the pin coordinates in a medial-lateral direction.

16. The system of claim 13, wherein the pin coordinates define the scaffold to have an anterior tail and an anterior horn, the anterior tail being at a transverse angle to the anterior horn to define a bend between the anterior tail and the anterior horn.

17. The method of claim 16, wherein the pin coordinates includes an anchor pin coordinate at the bend for the placement of an anchor pin.

18. The system of claim 16, wherein the pin coordinates define the scaffold to have a posterior tail and a posterior horn, the posterior tail being substantially in line with the posterior horn.

19. The system of claim 13, further comprising optimizing the first and second weighting factors by comparing the soft tissue data to dimensions of a simulated scaffold.

20. A non-transitory computing-device readable storage medium on which computing-device readable instructions of a program are stored, the instructions, when executed by one or more computing devices, causing the one or more computing devices to perform a method, the method comprising:
receiving soft tissue data corresponding to dimensions for a soft tissue, and a first and second weighting factor selected based on the dimensions of the soft tissue;
transforming the soft tissue data, based on the first and second weighting factors, into a plurality of pin coordinates in a multi-dimensional space defining a shape of the scaffold for use in fabricating the soft tissue implant; and
providing instructions to form the scaffold using weaving operations based on the pin coordinates.

* * * * *